United States Patent [19]

Burba, III et al.

[11] Patent Number: 4,727,167
[45] Date of Patent: Feb. 23, 1988

[54] INTERCALATIONS OF CRYSTALLINE LITHIUM ALUMINATES

[75] Inventors: John L. Burba, III, Angleton, Tex.; William C. Bauman, Midland, Mich.

[73] Assignee: The Dow Chemical Company, Midland, Mich.

[21] Appl. No.: 851,597

[22] Filed: Apr. 14, 1986

Related U.S. Application Data

[62] Division of Ser. No. 619,427, Jun. 11, 1984.

[51] Int. Cl.$^4$ .................................................. C07F 5/06
[52] U.S. Cl. .................................... 556/179; 252/184
[58] Field of Search ........................ 556/179; 252/184

[56] References Cited

U.S. PATENT DOCUMENTS

| | | | |
|---|---|---|---|
| 4,116,856 | 9/1978 | Lee et al. | 252/184 |
| 4,116,857 | 9/1978 | Lee et al. | 252/184 |
| 4,116,858 | 9/1978 | Lee et al. | 252/184 |
| 4,348,295 | 9/1982 | Burba, III | 252/184 |
| 4,348,296 | 9/1982 | Bauman et al. | 252/184 |
| 4,348,297 | 9/1982 | Bauman et al. | 252/184 |
| 4,461,714 | 7/1984 | Burba, III | 252/184 |
| 4,477,367 | 10/1984 | Burba, III | 252/184 |
| 4,540,509 | 9/1985 | Burba, III | 252/184 |

Primary Examiner—Helen M. S. Sneed

[57] ABSTRACT

Useful compositions are prepared by incorporating into organic materials, crystalline lithium aluminates which conform substantially to the empirical formula $$(LiA_x)_y \cdot 2Al(OH)_3 \cdot nH_2O$$

where A represents one or more anions and/or negative-valence radicals, where x represents a quantity of A ions and/or radicals sufficient to substantially satisfy the valence requirements of the Li, where y is a numerical value sufficient to maintain the crystalline structure, and where n represents the number of waters of hydration, if any.

6 Claims, No Drawings

INTERCALATIONS OF CRYSTALLINE LITHIUM ALUMINATES

This is a division of application Ser. No. 619,427, filed June 11, 1984.

BACKGROUND OF THE INVENTION

Crystalline compositions conforming generally to the empirical formula $Li^+(RCOO^-).2Al(OH)_3.nH_2O$, where $RCOO^-$ represents an organic acid anion, are disclosed, inter alia, in U.S. Pat. No. 4,348,295, U.S. Pat. No. 4,348,296, and U.S. Pat. No. 4,348,297. These 3 patents are incorporated herein by reference. Other relevant background patents are U.S. Pat. No. 4,116,856; U.S. Pat. No. 4,116,858; U.S. Pat. No. 4,159,311; U.S. Pat. No. 4,221,767; U.S. Pat. No. 4,347,327; U.S. Pat. No. 4,321,065; U.S. Pat. No. 4,376,100; and U.S. Pat. No. 4,381,349, all of which disclose related lithium aluminates.

Also disclosed are crystalline $LiX.2Al(OH)_3.nH_2O$ compounds and derivatives thereof, e.g., where the X anion represents OH, halide, halo acid, inorganic acid, organic acid and others. The compounds are referred to generally as "lithium aluminates" and are prepared, principally, by reacting lithium salts with hydrous alumina and forming crystalline $LiX.2Al(OH)_3.nH_2O$ which in some cases are of the "two-layer" variety and in some cases of the "three-layer" variety, depending on the particular method or materials employed. Methods for preparing these known crystalline lithium aluminates, of the $Li_x.2Al(OH)_3.nH_2O$ and $LiOH.2Al(OH)_3.nH_2O$ formulae, both 2-layer and 3-layer varieties, and anion exchanges or replacements in the crystals, are disclosed in the patents identified above especially those incorporated by reference.

SUMMARY OF THE INVENTION

It is within the purview of the present inventive concept, that crystalline compounds of the following empirical formula be combined with hydrocarbon and/or organic materials, said empirical formula being illustrated as

$(LiA_x)_y.2Al(OH)_3.nH_2O$ where A represents one or more anions and/or negative-valence radicals, including mixtures of such anions and/or negative-valence radicals, said anions and negative-valence radicals being monovalent or multivalent, where x represents a quantity of A ions and/or radicals sufficient to substantially satisfy the valence requirements of the Li, where n represents number of waters of hydration, and may be zero or more, especially about 0 to about 6, and where y is a numerical value sufficient to maintain the crystalline structure, especially about 0.5 to about 2.

In the above formula, the A moiety may represent only one kind, or a mixture of kinds, of anion or negative-valence radical, or may represent, e.g., at least one inorganic group along with at least one organic group.

DETAILED DESCRIPTIONS

As shown in the above patents which are incorporated herein by reference, hydrous alumina, represented by the formula $Al(OH)_3$, may be suspended in an ion exchange resin and then reacted with aq. LiOH at elevated temperature to form crystalline $LiOH.2Al(OH)_3$. It is understood, of course, that the so-formed crystalline aluminates, being in contact with water, have waters of hydration attached.

The said incorporated patents also disclose that the crystalline $LiOH.2Al(OH)_3$ is beneficially converted to $LiX.2Al(OH)_3$, where X is a halogen, i.e. Cl, Br, or I.

It is also disclosed that the crystalline $LiOH.2Al(OH)_3$, whether supported within or on a substrate, or prepared in the absence of a substrate, is beneficially converted to other lithium aluminates by reactions which replace the OH radicals with other anions or radicals.

Substrates in addition to ion exchange resins contemplated in accordance with the present invention include, e.g., inorganic substrates (which are substantially inert to the reactions involved in preparing the $(LiA_x)_y.2Al(OH)_3.nH_2O$), inert organic or inert polymeric substrates, and inert metallic substrates.

The "neat" preparations of the subject compounds, i.e. in the absence of a substrate, are also contemplated according to the present invention and usually allow larger aggregates or stacks of the crystals in the crystalline structure.

The anions (A) (including halide and hydroxyl) which are contemplated within the purview of the present invention include the anions of soluble inorganic acids, mineral acids, organic acids, or anions of the salts of such acids.

The anions of inorganic acids and mineral acids include, for example, $SO_4^{--}$, $HCO_3^-$, $BO_2^-$, $H_2PO_4^-$, $HPO_4^{--}$, $ClO_4^-$, $HCrO_4^-$, $NO_3^-$, $SO_3^{--}$, $HSO_3^-$, $NO_2^-$, $H_2AsO_4^-$, $HAsO_4^{--}$, $F^-$, $HS^-$, $ClO_3^-$, $H_2PO_3^-$, $HPO_3^{--}$, $H_3P_2O_7^-$, $MnO_4$, $H_2P_2O_7^{--}$, $HP_2O_7^{---}$, $NH_2SO_3^-$, $H_2PO_4^-$, $HPO_4^{--}$, $PO_4^{---}$, and the like.

The anions of organic acids may be derived, for example, from monobasic acids (RCOOH), dibasic acids (HOOC—COOH or HOOC—R—COOH), tribasic acids (HOOC—R(COOH)—COOH) where R is a substituted or unsubstituted hydrocarbon moiety, and other multibasic organic acids, such as ethylenediamine tetraacetic acid, acrylic acid polymers and copolymers, pyromellitic acid, and the like. Examples of monobasic acids are, for instance, formic acid, acetic acid, chloroacetic acid, dichloroacetic acid, trichloroacetic acid, acrylic acid, methacrylic acid, crotonic acid, butyric acid, propionic acid, tartaric acid, hexanoic acid, fatty acids (such as stearic acid), cyclic acids (such as benzoic acid), and the like. Examples of dibasic acids are, for instance, oxalic acid, malonic acid, fumaric acid, malic acid, maleic acid, succinic acid, terephthalic acid, pimelic acid, and the like. Citric acid is an example of a tribasic acid, $HOOCCH_2C(OH)(COOH)CH_2COOH$. Pyromellitic acid is an example of a quadribasic acid. Hydroxy carboxylic acids, such as glycollic acid, lactic acid, tartaric acid, and malic acid are within the purview of the present invention. Organic radicals with inorganic substituents, such as $CH_3SO_3^-$, $CH_3PO_3^{--}$, and $C_6H_{11}SO_3^-$ are within the purview of this invention.

Crystalline lithium aluminates conforming generally to the empirical formula $Li(RCOO)_y.2Al(OH)_3.nH_2O$, where RCOO represents a fatty acid anion, y is the number of Li atoms for each 2 Al atoms and n represents zero or a positive amount of waters of hydration, are prepared and are found to be useful as additives to organic fluids as thickeners, as viscosity control agents, as compatabilizers, and/or as dispersing agents. These aluminates are especially useful as additives to silicone oils and lubricants, synthetic oils and lubricants, organics, and hydrocarbons, most especially aliphatic hydrocarbons such as mineral oils, petroleum oils, motor oils, diesel oils, vegetable oils, and the like. In those aluminates wherein the fatty acid anion is derived from fatty acids having about 10 or more carbon atoms in the aliphatic carbon chain, or branched-chains, the aluminate is, itself, a useful grease or lubricant.

As used within the purview of this disclosure, the $Li(RCOO)_y.2Al(OH)_3.nH_2O$ compounds include the 2-layer and 3-layer varieties such as disclosed in U.S. Pat. No. 4,348,295 and U.S. Pat. No. 4,348,296. When written as $Li(RCOO)_y.2Al(OH)_3.nH_2O$, the subscript y is used (as in U.S. Pat. No. 4,348,297) to indicate the number of Li atoms per each 2Al atoms; the value of y is generally preferably about 1.0, but may be from about 0.5 to about 2, depending on how the crystals are prepared and on how much (if any) Li values have been leached or exchanged out of the crystals. In some cases the value of n can be virtually zero, indicating that waters of hydration are essentially absent, but in the absence of an intensive drying procedure, the value of n is usually in the range of about 0 to about 6.

The $RCOO^-$ anion in the lithium aluminate crystal may be any fatty acid wherein R represents an aliphatic carbon chain or branched-chain, having one or more carbon atoms. In those instances wherein it is desired that the aluminate compound be employed e.g. as a thickener, a gelling agent, a processing aid, a dispersing agent, and the like, in various oils, water dispersions, organic fluids, or as a grease or lubricant itself, it is preferred that the $RCOO^-$ anion contain more than 8 carbon atoms, more preferably 12 or more carbon atoms, most preferably about 14 to about 22 carbon atoms.

Polycarboxylic acid compounds, conforming essentially to the formula $R(COO^-)_x$, where x is a numerical value of at least 4, and where R is an organic moiety to which the carboxylic groups are attached, can be used.

The lithium aluminates of the present invention can also be added to polymers, waxes and paraffins which can be sufficiently fluidized at a temperature, generally, less than about 250°–300° C. to permit adequate mixing with the aluminate. These mixtures are useful, e.g., as lubricants, mold release agents, fire-retarding additives, and polymer additives. These lithium aluminates also serve to reinforce polymers or resins or other solidified materials to which they are added.

Of the fatty acids which are the source of the $RCOO^-$ anions of the crystalline lithium aluminates of the present invention, those which have from 1 to 8 carbon atoms in their molecule are at least partially soluble in water at 20° C., but those with 9 or more carbon atoms in their molecule are practically insoluble in water at 20° C. Thus, in preparing $Li(RCOO^-).2Al(OH)_3.nH_2O$ by the reaction of $CH_3(CH_2)_xCOOH$ (x is at least 7) with $LiOH.2Al(OH)_3.nH_2O$, a solvent or reaction medium other than water may be used. A convenient solvent or carrier is alcohol, such as isopropanol, though other solvents or carriers for the fatty acid may be used such as hexane, toluene, oils (e.g. mineral oils), ethers, halocarbons, silicone fluids, and the like. The fatty acid itself, so long as it is at a temperature at which it is molten, can serve as its own reaction medium. For example nonylic acid melts at about 12.5° C. and stearic acid melts at about 69° C.

A modicum of success is achieved by carrying out the long chain $RCOO^-$ intercalations in a water carrier if the fatty acid (molten or solid) is finely dispersed in the water, or a solution of the fatty acid is finely dispersed in water, and conducting the reaction with the crystalline lithium aluminate, preferably with stirring and at elevated temperature.

Of particular interest are $Li(RCOO^-)_y.2Al(OH)_3.nH_2O$ crystals wherein the $RCOO^-$ radical is from oleic acid, stearic acid, linoleic acid, linolenic acid, benzoic acid, and the like. These aluminates are thin platey structures which are substantially thermally stable to temperatures of about 300°–400° C. Some of them have about the same consistency of candle wax or soap and are useful as lubricants or greases at moderately high temperatures where many known hydrocarbon greases may lose their viscosity to the extent of being virtually ineffective as lubricants. Furthermore, these aluminates exhibit an ability to beneficially thicken hydrocarbon oils. For instance, 3-layer lithium oleate aluminate and 3-layer lithium stearate aluminate are successfully dispersed in mineral oil, motor oil, and diesel oil by adding about 30 gms. of the material to about 300 gms. of the oil by the action of an ultrasonic disperser operated about 12 minutes at a temperature of about 100° C. Stable water-in-oil dispersions can be prepared by dispersing lithium stearate aluminate in oils, e.g., diesel oil motor oil, mineral oil, hydraulic fluids, and the like, which contain, e.g. about 10% by volume $H_2O$.

Useful improvements in oil-based drilling fluids are found in the use of lithium stearate aluminate (and other $Li(RCOO^-)_y.2Al(OH)_3.nH_2O$ compounds) for thickening the hydrocarbon oils used for such drilling. Embodiments wherein the anions in the crystal are organic anions other than stearate are also useful in this type of activity.

The Process in General

Crystalline or amorphous hydrous alumina, denoted as $Al(OH)_3$, is reacted at elevated temperature to form crystalline $LiOH.2Al(OH)_3.nH_2O$ in an aqueous medium. The beginning hydrous alumina may be unsupported by a substrate, or may be supported on a substrate, or may be dispersed or suspended within a porous substrate. The reaction between the hydrous alumina and the LiOH may take place at room temperature but to assure that the reaction is substantially completed within a reasonable length of time, an elevated temperature of at least 50° C., preferably at least about 75° C. should be used. The amount of LiOH should not be in such excess that the aluminate is caused to precipitate outside the pores. The aqueous media may contain other ingredients and, if they are substantially inert or do not interfere with the desired reaction, are permissible. Insoluble, substantially inert particles may be present in the aqueous medium and may serve as a substrate for the $LiOH.2Al(OE)_3$ as it is formed. Choice of a substrate (if used) is dependent, of course, on the intended use of, or application of, the crystalline $LiOH.2Al(OH)_3.nE_2O$.

The present invention is not limited to a particular means for providing the beginning hydrous alumina for reaction with the LiOH. For example, the pores of a substrate may be substantially filled with $Al(OH)_3$ by growing seeds of $Al(OH)_3$ in the pores from an aqueous solution of sodium aluminate.

The crystalline $LiOH.2Al(OH)_3.nH_2O$ is then reacted in aqueous medium with anions or negative-valence radicals (A) having a valence of 1, 2, or 3 or more to form the $(LiA_x)_y.2Al(OH)_3.nH_2O$ compounds of the present invention. A monovalent anion or radical yields $(LiA)_y.2Al(OH)_3.nH_2O$. A divalent anion or radical yields $(LiA_{\frac{1}{2}})_y.2Al(OH)_3.nH_2O$. A trivalent anion or radical yields $(LiA_{\frac{1}{3}})_y.2Al(OH)_3.nH_2O$. Radicals of valence greater than 3 are similarly stoichiometrically balanced. The value of y is normally 1, but the actual value of y may vary over the range of about 0.5 to about 1.2, especially about 0.5 to about 1.2.

The so-prepared lithium aluminates are useful in selectively recovering $Li^+$ ions from solution if the amount of $LiA_x$ in the aluminate structure is first reduced to a lower concentration (but not completely removed), leaving space in the crystal for taking up $LiA_x$ salt until the crystal is once again "loaded" with $LiA_x$ salt.

The so-prepared lithium aluminates are also useful in exchanging of anions in aqueous solution, where an anion in solution replaces the anion in the crystal. For instance, where the A anion is the ascorbate radical of ascorbic acid (Vitamin C), the ascorbate anion is replaced by Cl in aqueous HCl, thereby providing ascorbic acid in the aqueous medium. The anion of ascorbic acid (a lactone) is formed by a keto-to-enol shift. The exchange of anions is also possible in non-aqueous systems, such as an alcohol, or in molten polymers or paraffins, such as polyethylene, polypropylene, polyvinylidene chloride, and the like.

It is well known that catalytic systems based on zeolite crystals are quite sensitive to inter crystalline spacing. The lithium aluminates used in the present invention provide an array of catalysts wherein the interplane or spacing of the crystalline aluminate structure is varied according to the size of the anion in the lithium aluminate.

The following examples are given to illustrate the preparation of compounds used in the present invention, but the invention is not limited to the particular embodiments illustrated.

EXAMPLE 1

An aqueous solution of $AlCl_3$ is reacted with $NH_4OH$ thereby precipitating $Al(OH)_3$. The $Al(OH)_3$ is washed with $H_2O$ to wash out $NH_4Cl$ and a slurry of the $Al(OH)_3$ in water is reacted with LiOH at elevated temperature (about 95° C.) to form crystalline $LiOH.2Al(OH)_3.nH_2O$.

A portion of the $LiOH.2Al(OH)_3.nH_2O$ slurried in water is titrated to pH 6 with $CCl_3COOH$ to form crystalline $Li(CCl_3COO).2Al(OH)_3.nH_2O$.

In a similar manner other lithium aluminates are prepared wherein the anion is $BO_2^-$, $NO_3^-$, $HCO_3^-$, $H_2PO_4^-$, $SO_4^{--}$, $F^-$, $CH_2ClCOO^-$, $CCl_2HCOO^-$, and the like.

X-ray diffraction patterns on the above products, and other products disclosed herein, indicate a crystalline material falling into the hexagonal crystal system with an interlayer distance of at least 7.5 Å. This distance is dependent on the size of the anion. These are 2- or 3-layer unit cell structures. The particle diameter is usually from about 150 Å to about 10000 Å. X-ray diffraction and scanning electron microscopic analysis have revealed its platelet structure. The ratio of the length to the thickness of these platelets can be between 1 and about 1500. White powders or particles are generally produced, but tinted or colored products are not precluded from this invention.

The number of waters of hydration in the crystalline aluminates used in the present invention is generally within the range of about 0 to about 6.

EXAMPLE 2

In one particular embodiment of the present invention, about 73 gms. of crystalline 3-layer $LiOH.2Al(OH)_3.nH_2O$ (where n is about 3) is dispersed in about 400 ml. of drum grade isopropanol and about 114 gms. of commercially available stearic acid (about 95% purity) is added. The mixture is stirred at about 40° C. for about 1 hour, then filtered and the product analyzed. By analysis it is found that lithium stearate aluminate is formed, conforming to the formula $Li(RCOO).2Al(OH)_3.nH_2O$ (where n is about 0), the product also containing a small amount of unreacted stearic acid which can be substantially removed by washing with isopropanol.

EXAMPLE 3

In another embodiment the procedure above is performed using crystalline 2-layer $LiOH.2Al(OH)_3.nH_2O$ and substantially the same results are obtained except for the difference in the number of crystal layers.

EXAMPLE 4

In yet another embodiment, the amount of stearic acid used is less than enough to replace all the OH anions in the $LiOH.2Al(OH)_3.nH_2O$ crystal, and the product made is substantially of the formula $Li(OH)_{\frac{1}{2}}(RCOO)_{\frac{1}{2}}.2Al(OH)_3.nH_2O$. This compound also finds utility as an additive to organics and hydrocarbons, e.g., as a thickener, an acid ion scavenger, a viscosity-adjusting agent, a lubrication agent, as emulsion stabilizers, as solids dispersing agents, and the like.

EXAMPLE 5

In addition to those fatty acids which are aliphatic, it has also been determined that aromatic acids and other cyclic acids can be used in forming $Li(RCOO).2Al(OH)_3$, e.g., benzoic, toluic, salicylic, gallic, cinnamic, and substituted acids such as these.

The crystalline lithium aluminate compounds described, supra, are uniformly mixed with various organic materials to form useful compositions wherein the organic materials may be:

1. a hydrocarbon, either liquid or solid;
2. an organic characterized as aliphatic, paraffinic, bicyclic, alicyclic, aromatic, alkane, alkene, arylene, isoalkylene, isoalkane, or isoalkene, including those which are substituted or unsubstituted, and including those which contain, as substituents, heteroatoms of the group consisting of N, S, O, Si, P, F, Cl, Br, and I;
3. a polymer or resin;
4. a silicone;
5. a thermoplastic material characterized as a wax, a paraffin, an olefin polymer, an olefin copolymer, a vinyl polymer, a vinyl copolymer, a polycarbonate, a polyalkyleneimene, a polyether, an epoxy, a polyurethane, a polysulfone, a polysiloxane, a polyterpene, a polyfluorocarbon, a polyimide, a silicone resin, a polyamide, a polyalkyleneoxide, or a polyacrylate;
6. a thermosetting material characterized as an epoxy, an epoxy-novolac, a vinylester, a polyurethane, a polyether, a glyptal resin, a phenolic resin, a ureaformaldehyde resin, or a urea condensation resin;

7. an organic material dissolved in a solvent;
8. an organic material containing at least a trace of halogen; or
9. an organic material which is liquid at ambient temperatures and pressures.

Furthermore, the anions or negative-valence radicals of the crystalline lithium aluminate compounds may be monovalent, of the group consisting of halide, hydroxyl, nitrate, carboxylic, alkoxide, phenolate, substituted phenolate, bicarbonate, dihydrogen phosphate, and bisulfate; and/or divalent, of the group consisting of sulfate, dicarboxylic, carbonate, monohydrogen phosphate, and organosulfate; and/or trivalent, of the group consisting of phosphate and tricarboxylic acid; and/or multivalent, of the group consisting of tetracarboxylic and polycarboxylic.

We claim:

1. Crystalline lithium aluminate compounds conforming essentially to the formula $$(Li^+ A^{-v}{}_{1/v})_y \cdot 2Al(OH)_3 \cdot nH_2O$$

wherein A represents a multivalent radical of a polycarboxylic compound, said A conforming to the formula $$R(COO^-)_x$$

where x is a numerical value of at least 4, and where R is an organic moiety to which the carboxylic groups are attached, where v is a valence of at least 4, where 1/v is a quantity of A ions or radicals sufficient to substantially satisfy the valence requirements of Li, where y is a numerical value at least sufficient to maintain the crystalline structure, and where n represents zero or the number of waters of hydration.

2. The crystalline compound of claim 1 wherein A represents the multivalent radical of ethylenediamine tetraacetic acid, pyromellitic acid, polyacrylic acid, or polymethacrylic acid.

3. The crystalline compound of claim 1 wherein A represents the multivalent radical of ethylenediamine tetraacetic acid.

4. The crystalline compound of claim 1 wherein A represents the multivalent radical of pyromellitic acid.

5. The crystalline compound of claim 1 wherein A represents the multivalent radical of polyacrylic acid.

6. The crystalline compound of claim 1 wherein A represents the multivalent radical of polymethacrylic acid.

* * * * *